US011213006B2

(12) United States Patent
Lepek et al.

(10) Patent No.: US 11,213,006 B2
(45) Date of Patent: Jan. 4, 2022

(54) RELEASE METHOD FOR INSECT DISTRIBUTION

(71) Applicant: Senecio Ltd., Kfar-Saba (IL)

(72) Inventors: Hanan Lepek, Kfar-Saba (IL); Rimon Arieli, Nesher (IL)

(73) Assignee: Senecio Ltd., Kfar-Saba (IL)

( * ) Notice: Subject to any disclaimer, the term of this patent is extended or adjusted under 35 U.S.C. 154(b) by 324 days.

(21) Appl. No.: 15/531,498

(22) PCT Filed: Dec. 3, 2015

(86) PCT No.: PCT/IL2015/051178
§ 371 (c)(1),
(2) Date: May 30, 2017

(87) PCT Pub. No.: WO2016/088127
PCT Pub. Date: Jun. 9, 2016

(65) Prior Publication Data
US 2017/0267346 A1    Sep. 21, 2017

Related U.S. Application Data

(60) Provisional application No. 62/087,584, filed on Dec. 4, 2014, provisional application No. 62/087,576, filed (Continued)

(51) Int. Cl.
*B64D 1/12* (2006.01)
*B64D 1/10* (2006.01)
(Continued)

(52) U.S. Cl.
CPC .............. *A01K 1/03* (2013.01); *A01K 67/033* (2013.01); *B64D 1/10* (2013.01); *B64D 1/12* (2013.01); *B64D 1/16* (2013.01)

(58) Field of Classification Search
CPC ... B64D 1/10; B64D 1/12; B64D 1/14; B64D 1/16
See application file for complete search history.

(56) References Cited

U.S. PATENT DOCUMENTS

| 1,124,579 A | 1/1915 | Ambursen |
| 1,957,075 A | 5/1934 | Morgensen, Jr. |

(Continued)

FOREIGN PATENT DOCUMENTS

| CA | 2654378 | 12/2007 |
| CN | 201585344 | 9/2010 |

(Continued)

OTHER PUBLICATIONS

Restriction Official Action dated May 11, 2018 From the US Patent and Trademark Office Re. U.S. Appl. No. 15/513,232. (7 Pages).

(Continued)

*Primary Examiner* — Tuongminh N Pham

(57) ABSTRACT

A diffuser for distributing insects such as mosquitoes from an aircraft, comprises a distribution tube connected to an insect source at a first end and open to the outside at a second end in a direction away from that of travel of the aircraft, for distribution of the insects; and a profile surrounding the second end, the profile being shaped to define a steadily changing airspeed. The pipe may be aligned with airflow at the point of exit of the pipe and protection may be provided around or just upstream of the exit to provide a point of minimal air velocity at the exit, the exit being the point of release of the insects.

22 Claims, 15 Drawing Sheets
(15 of 15 Drawing Sheet(s) Filed in Color)

Related U.S. Application Data on Dec. 4, 2014, provisional application No. 62/087,590, filed on Dec. 4, 2014.

(51) Int. Cl.
  *A01K 1/03* (2006.01)
  *A01K 67/033* (2006.01)
  *B64D 1/16* (2006.01)

(56) References Cited

U.S. PATENT DOCUMENTS

| | | | |
|---|---|---|---|
| 2,562,524 | A | 7/1951 | Burnum |
| 2,772,061 | A | 11/1956 | Sellers |
| 3,429,507 | A | 2/1969 | Jones |
| 3,705,659 | A | 12/1972 | Mackie |
| 4,260,108 | A | 4/1981 | Maedgen, Jr. |
| 4,430,044 | A | 2/1984 | Liljegren |
| 5,148,989 | A | 9/1992 | Skinner |
| 5,794,847 | A | 8/1998 | Stocker |
| 5,927,004 | A | 7/1999 | Stocker |
| 6,783,006 | B1 | 8/2004 | Sontag |
| 8,408,164 | B2 | 4/2013 | Robinson, Jr. |
| 9,314,010 | B2 | 4/2016 | Moreto et al. |
| 2002/0050659 | A1 | 5/2002 | Toreki et al. |
| 2002/0068358 | A1 | 6/2002 | Campbell et al. |
| 2003/0188698 | A1 | 10/2003 | Donaldson et al. |
| 2005/0009444 | A1 | 1/2005 | Davis et al. |
| 2005/0103276 | A1 | 5/2005 | Davis et al. |
| 2008/0009585 | A1 | 1/2008 | Catalfamo |
| 2009/0226116 | A1 | 9/2009 | Hill et al. |
| 2010/0001124 | A1 | 1/2010 | Feldman |
| 2011/0001011 | A1 | 1/2011 | Degiorgis et al. |
| 2011/0132278 | A1 | 6/2011 | Robinson, Jr. |
| 2011/0180003 | A1 | 7/2011 | Durnford et al. |
| 2014/0079652 | A1* | 3/2014 | Cooper ............. A61M 35/25 424/59 |
| 2014/0246545 | A1 | 9/2014 | Markov |
| 2015/0122182 | A1 | 5/2015 | Aldana et al. |
| 2016/0219887 | A1 | 8/2016 | Vickerson et al. |
| 2017/0267344 | A1 | 9/2017 | Lepek et al. |
| 2017/0297710 | A1 | 10/2017 | Lepek et al. |
| 2018/0332817 | A1 | 11/2018 | Lepek et al. |

FOREIGN PATENT DOCUMENTS

| | | |
|---|---|---|
| CN | 103202269 | 7/2013 |
| CN | 203446381 | 2/2014 |
| EP | 0210447 | 2/1987 |
| EP | 2266879 | 12/2010 |
| FR | 2583256 | 12/1986 |
| WO | WO 03/000047 | 1/2003 |
| WO | WO 03/087322 | 10/2003 |
| WO | WO 2010/148498 | 12/2010 |
| WO | WO 2011/076773 | 6/2011 |
| WO | WO 2014/086932 | 6/2014 |
| WO | WO 2016/046823 | 3/2016 |
| WO | WO 2016/088127 | 6/2016 |
| WO | WO 2016/088128 | 6/2016 |
| WO | WO 2016/088129 | 6/2016 |

OTHER PUBLICATIONS

Translation of Examination Report dated Oct. 24, 2017 From Ministerio de Comercio e Industrias, La Direccion General del Registro de la Propiedad Industrial, Departamento de Patentes de la Republica de Panama Re. Application No. 91657-01. (2 Pages).
Notification of Office Action and Search Report dated Dec. 28, 2018 From the National Intellectual Property Administration of the People's Republic of China Re. Application No. 201580075437.4 and Its Translation Into English. (15 Pages).
Notification of Office Action and Search Report dated Dec. 17, 2019 From the National Intellectual Property Administration of the People's Republic of China Re. Application No. 201580075737.2 and Its Translation of Office Action Into English. (11 Pages).
Official Action dated Jul. 29, 2019 From the US Patent and Trademark Office Re. U.S. Appl. No. 15/513,232. (26 pages).
Examination Report dated Sep. 3, 2019 From the Republica de Colombia, Superintendencia de Industria y Comercio Re. Application No. NC2017/0006718. (7 Pages).
Search Report and Opinion dated Aug. 21, 2019 From the Servico Publico Federal, Ministerio da Economia, Instituto Nacional da Propriedade Industrial do Brasil Re. Application No. BR112017011678-2 and Its Summary in English. (5 Pages).
Translation dated Oct. 17, 2019 of Examination Report dated Sep. 3, 2019 From the Republica de Colombia, Superintendencia de Industria y Comercio Re. Application No. NC2017/0006718. (13 Pages).
Search Report and the Written Opinion dated Nov. 2, 2017 From the Intellectual Property Office of Singapore, IPOS Re. Application No. 11201702171S. (9 Pages).
Translation of Status Report dated Sep. 15, 2017 From the Ministerio de Comercio e Industrias, La Direccion General del Registro de la Propiedad Industrial, Departamento de Patentes, DIGERPI, de la Republica de Panama Re. Application No. 91565-01. (3 Pages).
Status Report dated Sep. 15, 2017 From the Ministerio de Comercio e Industrias, La Direccion General del Registro de la Propiedad Industrial, Departamento de Patentes, DIGERPI, de la Republica de Panama Re. Application No. 91565-01. (2 Pages).
Examination Report dated Jul. 11, 2017 From the Republica de Colombia, Superintendencia de Industria y Comercio Re. Application No. NC2017/0006718 and Its Translation Into English. (5 Pages).
Examination Report dated Jul. 2, 2018 From the Australian Government, IP Australia Re. Application No. 2015323280. (4 Pages).
Notification of Office Action and Search Report dated Jul. 22, 2019 From the State Intellectual Property Office of the People's Republic of China Re. Application No. 201580055946.0 and Its Translation Into English.(10 Pages).
Restriction Official Action dated Aug. 23, 2019 From the US Patent and Trademark Office Re. Application No. 15/532,124. (9 pages).
Examination Report dated Jan. 22, 2019 From the Republica da Colombia, Superintendencia de Industria y Comercio Re. Application No. NC2017/0006718. (10 Pages).
Notification of Office Action and Search Report dated Nov. 27, 2018 From the State Intellectual Property Office of the People's Republic of China Re. Application No. 201580055946.0 and a Summary of the Notification of Office Action Into English. (6 Pages).
Examination Report dated Aug. 27, 2018 From the Republica de Colombia, Superintendencia de Industria y Comercio Re. Application No. NC2017/0003905 and Its Translation Into English. (10 Pages).
Communication Relating to the Results of the Partial International Search dated Mar. 7, 2016 From the International Searching Authority Re. Application No. PCT/IL2015/051180.
Communication Relating to the Results of the Partial International Search dated Mar. 7, 2016 From the International Searching Authority Re. Application No. PCT/IL2015/051181.
Examination Report dated May 4, 2017 From the Republica de Colombia, Superintendencia de Industria y Comercio Re. Application No. NC2017/0003905 and Its Translation Into English. (8 Pages).
International Preliminary Report on Patentability dated Jun. 15, 2017 From the International Preliminary Examining Authority Re. Application No. PCT/IL2015/051180. (10 Pages).
International Preliminary Report on Patentability dated Feb. 17, 2017 From the International Preliminary Examining Authority Re. Application No. PCT/IL2015/051178. (21 Pages).
International Preliminary Report on Patentability dated Feb. 17, 2017 From the International Preliminary Examining Authority Re. Application No. PCT/IL2015/051181. (20 Pages).
International Preliminary Report on Patentability dated Dec. 21, 2016 From the International Preliminary Examining Authority Re. Application No. PCT/IL2015/050964. (11 Pages).

(56) References Cited

OTHER PUBLICATIONS

International Search Report and the Written Opinion dated Jun. 1, 2016 From the International Searching Authority Re. Application No. PCT/IL2015/051181.
International Search Report and the Written Opinion dated Mar. 4, 2016 From the International Searching Authority Re. Application No. PCT/IL2015/051178.
International Search Report and the Written Opinion dated Aug. 17, 2016 From the International Searching Authority Re. Application No. PCT/IL2015/051181.
International Search Report and the Written Opinion dated Apr. 29, 2016 From the International Searching Authority Re. Application No. PCT/IL2015/051180.
International Search Report and the Written Opinion dated Jan. 29, 2016 From the International Searching Authority Re. Application No. PCT/IL2015/050964.
Written Opinion dated Dec. 13, 2016 From the International Preliminary Examining Authority Re. Application No. PCT/IL2015/051181. (10 Pages).
Written Opinion dated Aug. 24, 2016 From the International Preliminary Examining Authority Re. Application No. PCT/IL2015/050964.
Written Opinion dated Oct. 25, 2016 From the International Preliminary Examining Authority Re. Application No. PCT/IL2015/051178. (6 Pages).
Dame et al. "Historical Applications of Induced Sterilisation in filed Populations of Mosquitoes", Malaria Journal, 8(Suppl.2/S2): 1-10, Nov. 16, 2009.
Patterson et al. "The Sterile-Male Technique for Control of Mosquitos: A Field Cage Study With *Anopheles quadrimaculatus*", The Florida Entomologist, 51(2): 77-82, Jun. 1968.
Advisory Action Before the Filing of An Appeal Brief dated Jan. 21, 2020 From the US Patent and Trademark Office Re. U.S. Appl. No. 15/513,232. (5pages).
Communication Pursuant to Article 94(3) EPC dated Jan. 3, 2020 From the European Patent Office Re. Application No. 15820296.0. (4 Pages).
Examination Report dated Jul. 6, 2017 From the Republica de Colombia, Superintendencia de Industria y Comercio Re. Application No. NC2017/0006705 and Its Translation Into English. (5 Pages).
Translation dated Jan. 30, 2019 of Examination Report dated Oct. 22, 2018 From the Republica da Colombia, Superintendencia de Industria y Comercio Re. Application No. NC2017/0006718. (7 Pages).
Translation dated Jan. 31, 2019 of Notification of Office Action and Search Report dated Nov. 27, 2018 From the State Intellectual Property Office of the People's Republic of China Re. Application No. 201580055946.0. (4 Pages).
Communication Pursuant to Article 94(3) EPC dated Apr. 16, 2018 From the European Patent Office Re. Application No. 15791374.0. (4 Pages).
Examination Report dated Aug. 15, 2017 From the Instituto Mexicano de la Propiedad Industrial, IMPI Re. Application No. MX/a/2017/007267. (2 Pages).
Search Report dated Oct. 24, 2017 From the Ministerio de Comercio e Industrias, La Direccion General del Registro de la Propiedad Industrial, Departamento de Patentes de la Republica de Panama, DIGERPI Re. Application No. 91656-01 and Its Translation Into English. (5 Pages).
Official Action dated May 15, 2019 From the US Patent and Trademark Office Re. U.S. Appl. No. 15/531,750. (65 pages).
Notice of Eligibility for Grant: Search Report and Examination Report dated Apr. 3, 2018 From the Intellectual Property Office of Singapore Re. Application No. 11201704330W. (8 Pages).
Official Action dated Nov. 15, 2018 From the US Patent and Trademark Office Re. U.S. Appl. No. 15/513,232. (45 pages).
Notice of Eligibility for Grant and Examination Report dated Apr. 19, 208 From the Intellectual Property Office of Singapore, IPOS Re. Application No. 11201702171S. (6 Pages).

Official Action dated Nov. 26, 2019 From the US Patent and Trademark Office Re. U.S. Appl. No. 15/532,124. (73 pages).
Notice of Acceptance dated Jun. 25, 2019 From the Australian Government, IP Australia Re. Application No. 2015323280. (6 Pages).
Examination Report dated Oct. 24, 2017 From Ministerio de Comercio e Industrias, La Direccion General del Registro de la Propiedad Industrial, Departamento de Patentes de la Republica de Panama Re. Application No. 91657-01. (2 Pages).
Official Action dated Jun. 4, 2020 from the US Patent and Trademark Office Re. U.S. Appl. No. 15/532,124. (18 pages).
Search Report and Explanations dated May 5, 2020 From the Servico Publico Federal, Ministerio da Economia, Instituto National da Propriedade Industrial do Brasil Re. Application No. BR112017005768-9 and Its Summary in English. (5 Pages).
Official Action dated May 29, 2020 from the US Patent and Trademark Office Re. U.S. Appl. No. 15/513,232. (23 pages).
Examination Report Under Sections 12 & 13 of the Patents Act, 1970 and the Patents Rules, 2003 dated Jul. 21, 2020 From the Government of India, Intellectual Property India, Patents, Designs, Trade Marks, Geographical Indications, The Patent Office Re. Application No. 201727012659. (6 Pages).
Office Action dated Oct. 6, 2020 From the Israel Patent Office Re. Application No. 252635 and Its Translation Into English. (6 Pages).
Translation dated Oct. 11, 2020 of Examination Report dated Sep. 10, 2020 From the Republica de Colombia, Superintendencia de Industria y Comercio Re. Application No. NC2017/0006718. (7 Pages).
Communication Pursuant to Article 94(3) EPC dated Oct. 14, 2020 From the European Patent Office Re. Application No. 15820296.0. (5 Pages).
Examination and Search Report dated Sep. 10, 2020 From the Republica de Colombia, Superintendencia de Industria y Comercio Re. Application No. NC2017/0006718. (7 Pages).
Translation dated Sep. 30, 2020 of Examination Report dated Aug. 25, 2020 From the Instituto Mexicano de la Propiedad Industrial, IMPI, Secretario de Economia, Direccion Divisional de Patentes Re. Application No. MX/a/2017/003733. (5 Pages).
Examination Report dated Mar. 11, 2020 From the Republica de Colombia, Superintendencia de Industria y Comercio Re. Application No. NC2017/0006718 and Its Translation Into English. (12 Pages).
Examination Report dated Sep. 23, 2020 From the Republica de Costa Rica, Registro Nacional, Registro de la Propiedad Intelectual Re. Application No. 2017-0306 and Its Translation Into English. (14 Pages).
Notification of Office Action dated Oct. 14, 2020 From the National Intellectual Property Administration of the People's Republic of China Re. Application No. 201580075737.2 and Its Summary in English. (9 Pages).
Examination Report dated Aug. 25, 2020 From the Instituto Mexicano de la Propiedad Industrial, IMPI, Secretario de Economia, Direccion Divisional de Patentes Re. Application No. MX/a/2017/003733.
Official Action dated Sep. 15, 2020 from the US Patent and Trademark Office Re. U.S. Appl. No. 15/532,124. (15 pages).
Examination Report dated Mar. 18, 2021 From the Australian Government, IP Australia Re. Application No. 2015356564. (6 Pages).
Examination Report dated Mar. 22, 2021 From the Australian Government, IP Australia Re. Application No. 2015356566. (5 Pages).
Examination Report Under Sections 12 & 13 of the Patents Act, 1970 and the Patents Rules, 2003 dated Mar. 18, 2021 From the Government of India, Intellectual Property India, Patents, Designs, Trade Marks, Geographical Indications, The Patent Office Re. Application No. 201727022663. (9 Pages).
Final Official Action dated Mar. 1, 2021 From the US Patent and Trademark Office Re. U.S. Appl. No. 15/513,232. (37 Pages).
Final Official Action dated Feb. 22, 2021 From the US Patent and Trademark Office Re. U.S. Appl. No. 15/532,124. (24 Pages).

(56) References Cited

OTHER PUBLICATIONS

Notification of Office Action and dated Feb. 5, 2021 From the State Intellectual Property Office of the People's Republic of China Re. Application No. 201580075737.2 Its Summary Into English. (3 Pages).

Examination Report dated Jul. 23, 2021 From the Republica De Columbial, Superintendencia De Industria Y Comercio Re. Application No. NC2017/0006718. (8 Pages).

Translation dated Aug. 13, 2021 of Examination Report dated Jul. 26, 2021 From the Republica de Colombia, Superintendencia de Industria y Comercio Re. Application No. NC2017/0006718. (17 Pages).

Communication Pursuant to Article 94(3) EPC dated Jun. 28, 2021 From the European Patent Office Re. Application No. 15820296.0. (6 Pages).

Official Action dated Jun. 24, 2021 From the US Patent and Trademark Office Re. U.S. Appl. No. 15/532,124. (14 Pages).

Translation dated Jul. 13, 2021 of Examination Report dated Jun. 25, 2021 From the Instituto Mexicano de la Propiedad Industrial, IMPI, Secretaria de Economia, Direccion Divisional de Patentes Re. Application No. MX/a/2017/007252. (5 Pages).

\* cited by examiner

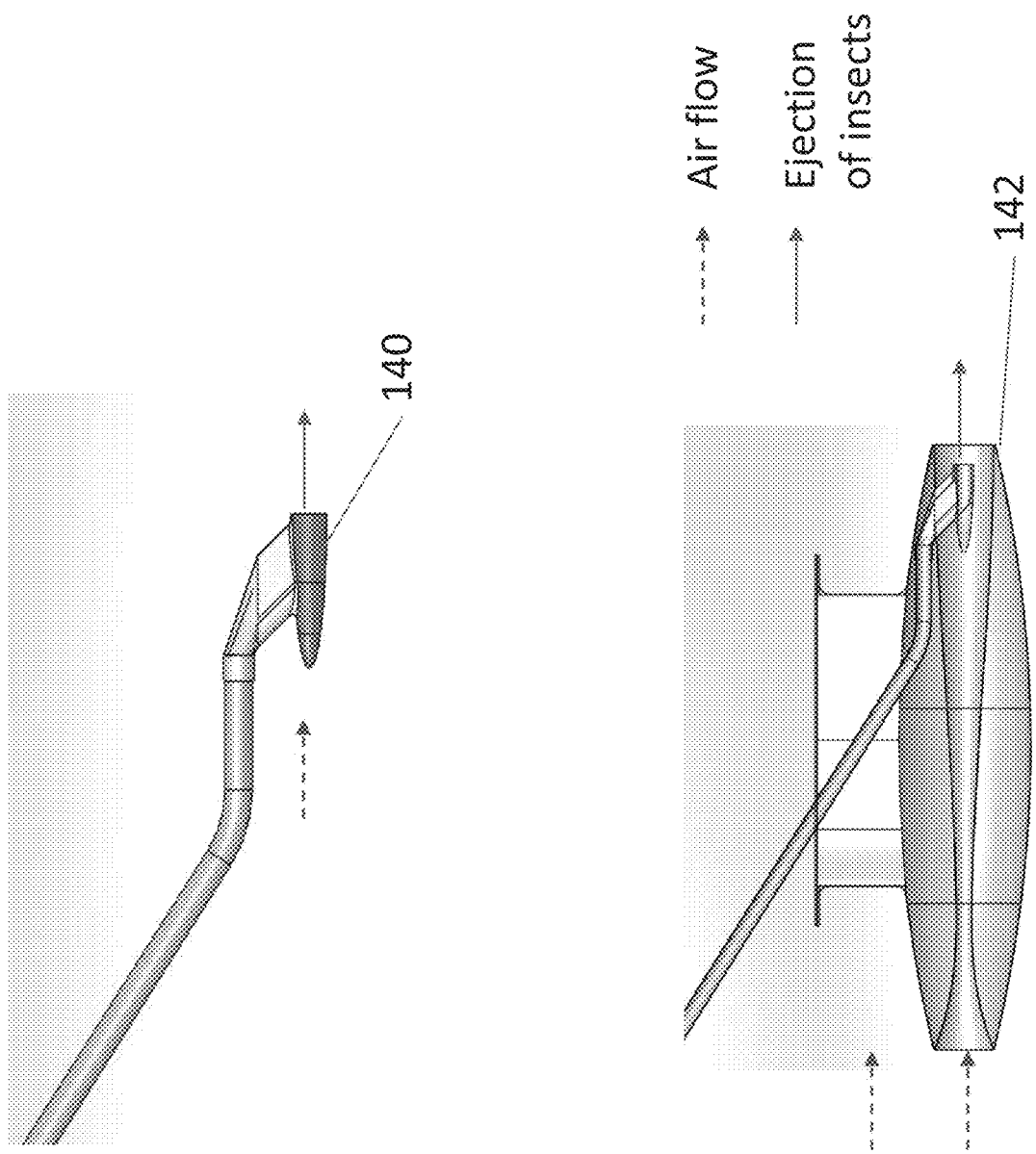

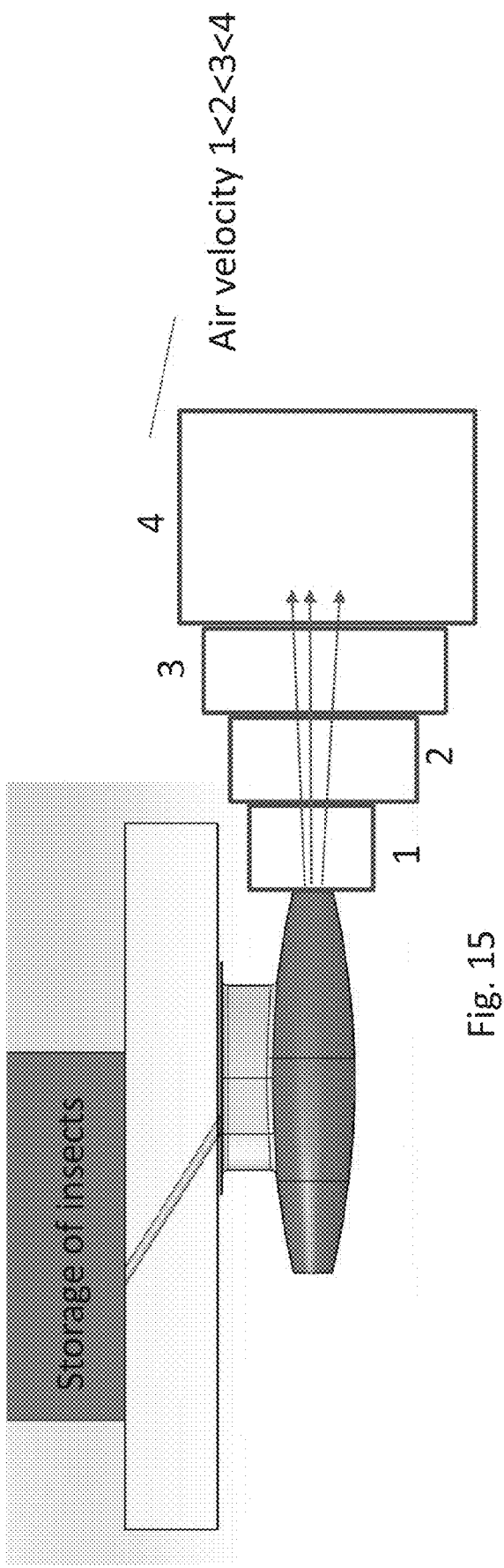
Fig. 15 in the Americas, Africa and
RELEASE METHOD FOR INSECT DISTRIBUTION

RELATED APPLICATIONS

This application is a National Phase of PCT Patent Application No. PCT/IL2015/051178 having International filing date of Dec. 3, 2015, which claims the benefit of priority under 35 USC § 119(e) of U.S. Provisional Patent Application Nos. 62/087,584, 62/087,576 and 62/087,590, all filed on Dec. 4, 2014. The contents of the above applications are all incorporated by reference as if fully set forth herein in their entirety.

FIELD AND BACKGROUND OF THE INVENTION

The present invention, in some embodiments thereof, relates to a method and apparatus for artificial distribution of insects and, more particularly, but not exclusively, to the distribution of insects as part of disease control programs, vector control programs, pollination programs and the like.

There are today large regions in the Americas, Africa and Asia that suffer from vector-born diseases transferred by insects, in particular, mosquitoes. The diseases include in particular Dengue fever, Chikungunya and Malaria, which are infectious disease carried and spread by bites from female mosquitoes.

There have been many attempts at a safe and effective means to control vector-born disease, specifically Dengue and Malaria, over sizeable regions, including urban areas by controlling the mosquito population. One method is to release sterile males.

The sterile males mate with the females in place of fertile males and in this way prevent reproduction.

A problem with the attempts has been effective distribution of the sterile males. It is not possible to release the insects from aircraft as is done with chemicals and crop dusting, as the airspeeds and wind shear involved generally kill the insects. This is particularly true of mosquitoes which are relatively fragile. Land-based distribution on the other hand is very labour-intensive and it is very difficult and costly to get a reasonable distribution of males, into all of the kinds of places where the mosquitoes congregate. One method that is used involves slow release of sterile males from a cage on a slowly moving vehicle. However this limits the release to areas that have vehicle access, and mosquito distribution pays little regard to vehicle access. A further difficulty is that release is limited to a few hours a day when the mosquitoes are active. Attempting to release mosquitoes at other times is ineffective.

Also, when releasing mosquitoes from open cages, it is difficult to control and change the density at which the mosquitoes are released with regard to the level of risk per given area.

The need for aerial release systems is described in the literature. The following are selected quotes:

The Sterile Insect Technique for Controlling Populations of *Aedes albopictus* (Diptera: Culicidae) on Reunion Island Mating Vigour of Sterilized Males states that provided suitable aerial release systems can be developed and the surface of the treated area is large enough, aerial releases would ensure a cost-effective area-wide coverage.

The Sterile Insect Technique: can established technology beat malaria? International Atomic Energy Agency, 2006, stated, "Aerial releases, although never tried with mosquitoes, have a number of potential benefits over ground releases. The release sites can be further away from the facilities, extending the geographical scope of the operation greatly. The need for good ground access to the field sites is no longer valid for daily releases, although for monitoring purposes it would still be desired. In addition, the number of staff required for aerial releases is lower and aerial releases can benefit from existing on-board navigation equipment to accurately release the mosquitoes in the designated areas . . . . However, unlike the robust medfly, mosquitoes are rather fragile creatures. Handling, packing and release methods for mosquitoes need to be developed and tested to assess the impact of aerial release on male behaviour and longevity . . . ".

Historical applications of induced sterilisation in field populations of mosquitoes, David A Dame, Christopher F Curtis, Mark Q Benedict, Alan S Robinson and Bart G J Knols, 2009 states " . . . Sterile mosquito releases conducted to date have relied on ground release. Relatively simple packaging, transport methodology, release containers and shelters have been devised for pupal and adult releases, but no work has been initiated on methods of aerial distribution. Certainly, in urban programmes ground release might suffice, but the availability of satisfactory aerial release methods could provide timelier and more effective distribution with reduced opportunity for pre-release damage to the sterile males. Production and release of millions per day will demand expedited delivery mechanisms to prevent losses in quality and competitiveness".

At the present time there are two basic systems for aerial release of insects. These are the bag release and chilled fly release systems. However these tend to be used for relatively hardy insects such as fruit flies and are less useful for mosquitoes which are relatively fragile.

The bag release is a relatively simple process in which flies emerge from within sealed paper bags which are ripped open and then dropped out of the aircraft. For example the bags may be ripped open manually and thrown out of the window, or can be thrown down an exit chute, coming into contact with hooks or knives located at the end of the chute upon exiting the aircraft.

The resulting litter generally biodegrades, but is not environment-friendly in dry climates where the degradation process is slow.

The paper bags serve to increase the surface area within the container thereby reducing competition for space between the enclosed individuals.

The flies generally remain in the bags until reaching the ground, and then emerge out of the tear, at this point being exposed to the risk of being eaten by predators.

The chilled adult release system works as follows. At the release center the insects are placed into room-size refrigerators and chilled to 4° C. until they fall down to the bottom of PARC boxes in a phase known as the knockdown phase. The chilled insects are then collected into a chill-box which is carried to the release airplane, a box holding as many as five million sterile insects. Once in the plane, the box is attached to a cooler that keeps the insects motionless during the release period, also making the flies less active, achieving a more even distribution into the environment. The flies drop from the bottom of the chill-box into an auger system, which moves them through a chute located on the underside of the airplane fuselage. The release rate, of insects per unit area, can be controlled via the revolution speed of the auger system. Insect mortality in this system is negligible and dispersal is satisfactory, however the system is only suitable for flies, which are relatively robust insects, and, as mentioned, cannot be used on the more fragile insects such as mosquitoes.

Aircraft distribution device disclosed in applicant's US Provisional patent application U.S. 62/053,242 filed Sep. 22, 2014, Method and Apparatus for Artificial Distribution of Insects, describe a system for releasing fragile insects typically from small agricultural plane travelling typically at 120 km/hr.

The small velocity region described may not present the desired low velocities for an airplane travelling more than 120 km/hr.

The size of the suggested device cannot be unlimited increased if it is intended to be mounted on low speed agricultural airplanes, in order to obtain better results (small velocity region also for higher airplane travelling velocity) since increasing the size of the device intended for use on small agricultural airplanes, may effect on the safety of the flight and performance of the aircraft.

SUMMARY OF THE INVENTION

The present embodiments may involve setting up a transition volume of gradually changing air velocity between the aircraft and the ambient air so that the insects are not exposed to violent wind shears the moment they exit the aircraft. One way of achieving such a transition volume is to release the insects using a slight overpressure, from within a slender, elongated central body placed within a nozzle with an axisymmetric pod like geometry.

According to a first embodiment of the present invention there is provided a diffuser for distributing insects from an aircraft, the aircraft having an inside and an outside, and comprising:
at least one distribution tube connected to an insect source at a first end and open to the outside at a second end in a direction away from the direction of travel of the aircraft, for distribution of the insects; and
a profile surrounding the second end, the profile being shaped to define a steadily changing airspeed.

In an embodiment, the opening is located in respect of the shaped profile at an airspeed minimum location.

In an embodiment, the steadily changing airspeed comprises a gradient of steadily accelerating airspeed away from the distribution tube in the direction away from the direction of travel of the aircraft.

In an embodiment, the profile is shaped to provide gradual aerodynamic deceleration towards the second end following the gradient of steadily accelerating airspeed.

In an embodiment, a blunt obstacle is located upwind of the second end, thus generating the airspeed minimum at the second end.

An embodiment may comprise a nozzle shape surrounding the second end;
and a tube shield surrounding the second end within the nozzle, the tube shield having an aerofoil-shaped cross section, the tube cover and the nozzle together forming the profile.

The diffuser may be an aircraft pod, and the aircraft pod may provide a nozzle for the insects.

In an embodiment, the pod comprises a substantially circular cross section.

In an embodiment, the pod is for mounting under an aircraft fuselage or under an aircraft wing.

In an embodiment, the insect source is contained within the pod along with the diffuser.

In an embodiment, the pod comprises a subsonic converging-diverging nozzle shape.

In an embodiment, the pod comprises a bi-cubic polynomial internal contour.

In an embodiment, the pod comprises an elliptical external shape.

In an embodiment, the aerofoil shape is an NACA standard shape, which may more particularly be the NACA 0018 standard shape.

In an embodiment, the tube shield is positioned within the pod such that a smooth external contour of the standard shape limits flow separation to the near wake of the blunt trailing edge section of the nozzle.

In an embodiment, the insect source is provided with an overpressure.

In an embodiment, the overpressure is such as to provide an air velocity exiting the tube at the second end of substantially 1 m/s (one meter per second).

In an embodiment, the nozzle is cubic.

In an embodiment, the insects being distributed comprise relatively fragile insects being unable to bear a wind shear in excess of 60 km/h.

In an embodiment, the insects being distributed comprise male insects.

In an embodiment, the insects being distributed comprise sterile male mosquitoes.

The present embodiments may be used to diffuse from an aircraft travelling in excess of 110 kmh.

According to a second aspect of the present invention there is provided a diffuser for distributing insects from an aircraft, the aircraft having an inside and an outside, and comprising:
at least one distribution tube connected to an insect source at a first end and open to the outside at a second end in a direction away from the direction of travel of the aircraft, for distribution of the insects; and
a profile surrounding the second end, the profile being shaped to define an airflow direction that is tangential to streamlines local to the second end.

The diffuser may be being mounted to an aircraft by an aircraft mounting, wherein the profile is formed from a combination of a tube shield protecting the second end, a nozzle and the mounting.

According to a third aspect of the present invention there is provided a method of aerial distribution of fragile insects comprising:
releasing insects into a release tube having an exit into ambient air;
aligning the release tube with an airstream direction around the exit; and releasing the insects through the exit into the ambient air.

The method may further comprise placing a shield upstream of the exit to shield the exit from airflow.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

In the drawings:

FIG. 12 is a simplified diagram showing two structures of the pod of FIG. 2 for different air speeds;

FIG. 15 is a simplified schematic diagram illustrating an insect distribution example according to the present embodiments, and showing associated velocities.

DESCRIPTION OF SPECIFIC EMBODIMENTS OF THE INVENTION

Figure 1:
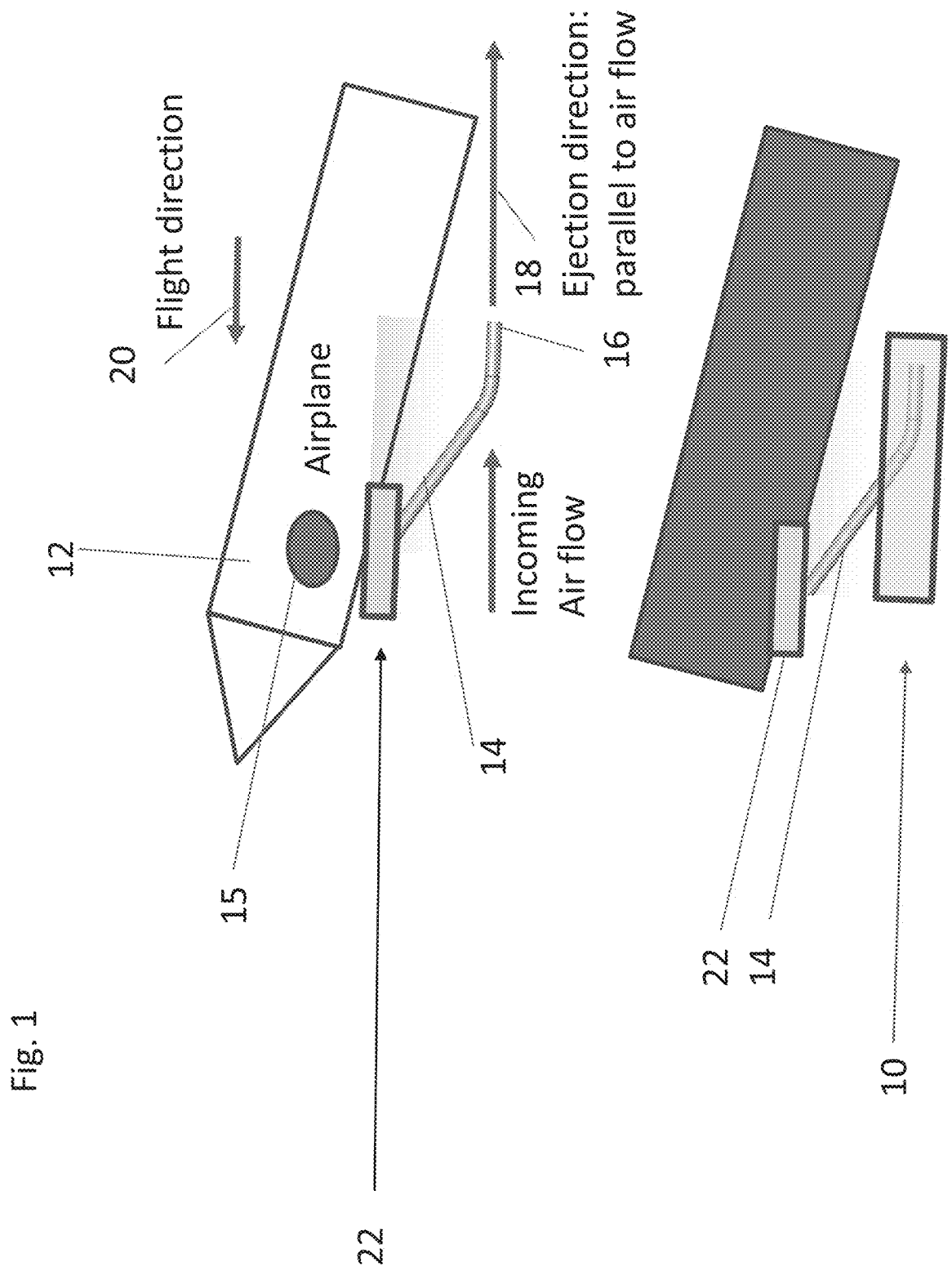
FIG. 1 is a schematic view of an insect ejection mechanism according to an embodiment of the present invention.

The present invention, in some embodiments thereof, relates to a method and apparatus for artificial distribution of insects and, more particularly, but not exclusively, to the distribution of insects as part of disease control programs, vector control programs, pollination programs and the like.

Mosquitoes are fragile insects and thus if introduced directly to aeronautical windspeeds upon release, the mortality rate will be very high. The present embodiments may provide the insects with a gradual change in airspeeds, thus reducing the mortality rate and making the release process more efficient. The effect is achieved first of all by releasing the insects behind the aircraft in a direction anti-parallel to the direction of travel, and secondly by providing shielding around the release point to provide a lower windspeed at the release point. In one embodiment the release point is surrounded by a nozzle and in a further embodiment the release point is placed along the length of a shaped profile which is initially narrow and then gradually widens. The opening is placed at a point along that profile which is determined to have a lowest windspeed.

The mosquitoes may thus be released backwards along the flight path. However, the airplane itself and some of its subsystems may affect the flow direction in the vicinity of the airplane. Furthermore, mosquitoes are very sensitive to wind gusts. Therefore, the present embodiments may provide local shielding for the mosquito outlet, and may align the mosquito delivery direction as close as possible to local windflow direction. Moreover, the embodiments may ensure that the velocity gradient along the mosquito delivery path is kept small.

In general, best results are obtained when the release direction is collinear with local airflow. When the device is mounted on a moving aerial vehicle, then it may be mounted such that the mounting compensates for any angle between the vehicle and the air flow so the actual release is still collinear with the air flow. That is to say, when the device is mounted on an airplane, its orientation relative to the aircraft waterline should be such that the release direction is tangential to local streamlines.

The pod of the present embodiments places an object just behind the insect release point which blocks the inflowing air, and creates a local volume with low air flow, which then gradually increases in all directions, that is in all three of the X-Y-Z directions.

The above is a description of the geometry in general, and depending on the performance required, how low an airflow is needed, or how fast a flow gradient is required, different geometries may be applied as seen in the figures. More particularly, low air speed in the vicinity of the delivery port is obtained either by gradual aerodynamic deceleration, or by the presence of a blunt obstacle ahead of the delivery region, thus generating a local airflow equivalent of a dead water region.

In one embodiment, the insects are pushed out of the aircraft to the release point using air pressure. In such a case the insects may remain as long as possible along the path anti-parallel to the airflow, in which the gradient is the smallest. That is to say the mosquito expulsion through the feeding tube is at a small longitudinal velocity that further helps in diminishing the relative air speed between the external air stream and the mosquitoes.

The axisymmetric device may be used for the delivery of fragile materials, such as mosquitoes for example, at higher speeds that the typical operational speed of regular agricultural aircraft, say about 32 m/s which are about 100 kph.

The overall configuration consists of a hollow converging-diverging axisymmetric nozzle. The external or shield may resemble an ellipsoidal shape in the longitudinal direction. The cover may have a round cross section perpendicular to the x-axis.

The device of the present embodiments may share some functionality and operational procedures with the two-dimensional system described in US Provisional patent application U.S. 62/053,242 filed Sep. 22, 2014, Method and Apparatus for Artificial Distribution of Insects ("U.S. 62/053,242"). The present unit may also have a tube cover or shield unit to launch the materials from within directly into a low velocity region, and connectivity with storage elements to obtain the insects. The present embodiments however have an axisymmetric pod like geometry, as will be discussed in greater detail herein. The fact the device is axisymmetric provides the ability to increase the ratio between the device surface area on the exit point and the device surface area at the entrance point. While for the two dimensional device described in U.S. 62/053,242 the ratio of the surface areas corresponds to the ratio in the heights between the upper and lower device edges of the exit and throat sections, the case of the axisymmetric pod like geometry, is somewhat different. In this case the influencing parameter is the ratio between the area at the exit to the throat area as will be discussed in greater detail below. A difference between a two-dimensional nozzle and an axisymmetric one may be that for similar height differences between the exit and the throat, the corresponding area ratio in the axisymmetric case is proportional to the square of the height ratio.

Therefore, in the axisymmetric case a considerably higher area ratio is achievable so that local air velocity at the pod exit might be further reduced. Thus, an axisymmetric configuration provides the ability to further increase the device size (e.g. length and diameter), achieving the required transition from high speed to low speed for the insects being released, while preventing flow separations along the nozzle walls. The proposed axisymmetric pod like geometry device may be preferred over the two-dimensional device described in U.S. 62/053,242 in cases where the airplane is travelling at a typical velocity higher than 140 km/hr and given there is sufficient ground clearance from either the fuselage or the wing for mounting the pod like structure.

The length of the axisymmetric device might lie in the range of 0.800 m<Length<1.600 m (depends on flight conditions). The maximum diameter of the device will be 0.180 m<$D_{max}$<0.240 m. The internal hub (shape and longitudinal location) is specially design to minimize flow separations and pressure loses in the diverging part of the nozzle.

The fragile insects to be released may arrive from storage tanks connected with distribution pipes from the storage tanks towards the release point.

If there is adequate room for insect storage tanks inside the fuselage, then the fuselage may be used, and adequate pipes for the delivery of the mosquitoes to the "hub" inside the nozzle are provided.

Alternatively, tanks may be attached to the sides of the delivery nozzle. In this case the external contour of the pod may be of an elliptic shape providing aerodynamic structure for the pod with the attached tanks.

The tanks may be stored within the external contour—located between the inner contour of the pod and the external contour of the pod with an external contour of an elliptic shape. The shape of the tanks may be rectangular storage units, subject to being fitted inside the external contour. The external contour may have doors in order to change, unload and load the storage units within the external contour with insects such as mosquitoes.

In an embodiment, the tanks may form the external contour of the pod.

Each tank or storage device may have a propulsion unit to push the insects away towards the tube cover for the release point.

The outlet of the tank may have a shutter to be opened in sync with the operation of the propulsion unit for releasing the insects out of their tanks.

The release from the tanks can be continuous being controlled by a central controller.

Figure 9:
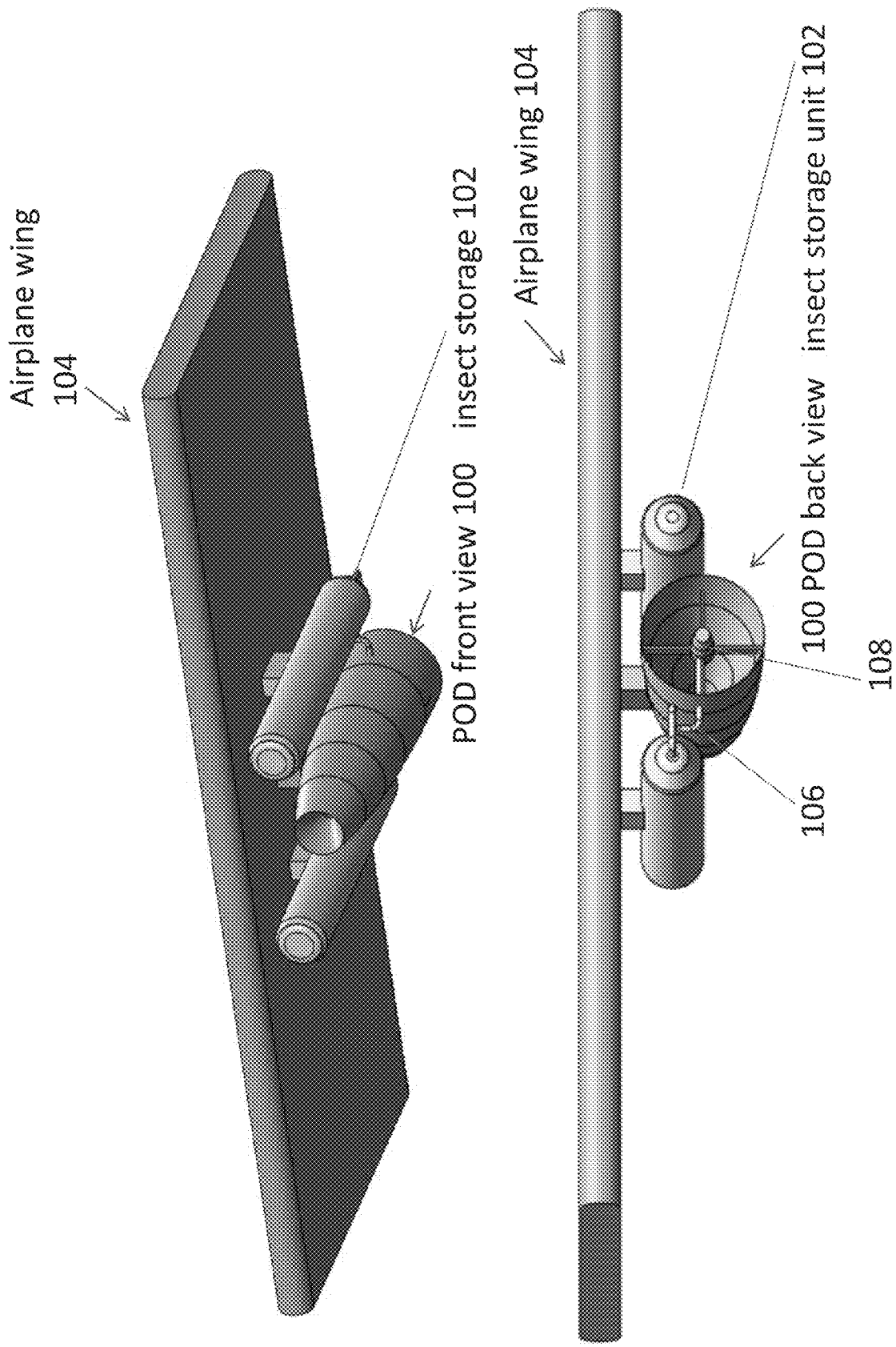
FIG. 9 is a schematic airplane wing view with an axisymmetric pod shape of FIG. 2 mounted below the wing and fragile insects storage cells mounted next to the pod with connecting pipes.

In another embodiment, storage is within cassettes adjacent to the pod, connected with pipe delivery system from the storage units to the tube cover for the release point, as seen in FIG. 9.

The cross-section of the insect outlet may be round but may alternatively be asymmetric and may be a three-dimensional construction. The reasons for the constructions being asymmetric may include physical fitting of the components within the pod, clearance from the ground, etc.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a simplified schematic diagram illustrating a diffuser 10 attached to an aircraft 12 for distributing insects from an aircraft. A distribution tube 14 is attached to an insect source 15 at one end and open to the outside at a second end 16 to release the insects in the direction of arrow 18 which points in a direction away from the direction of travel of the aircraft, arrow 20. Connector 22 connects the diffuser to the aircraft.

The insects, for example mosquitoes, are released at release point 16 in the direction of arrow 18, which is aligned to be along the airstream at the given locality.

Figure 2:
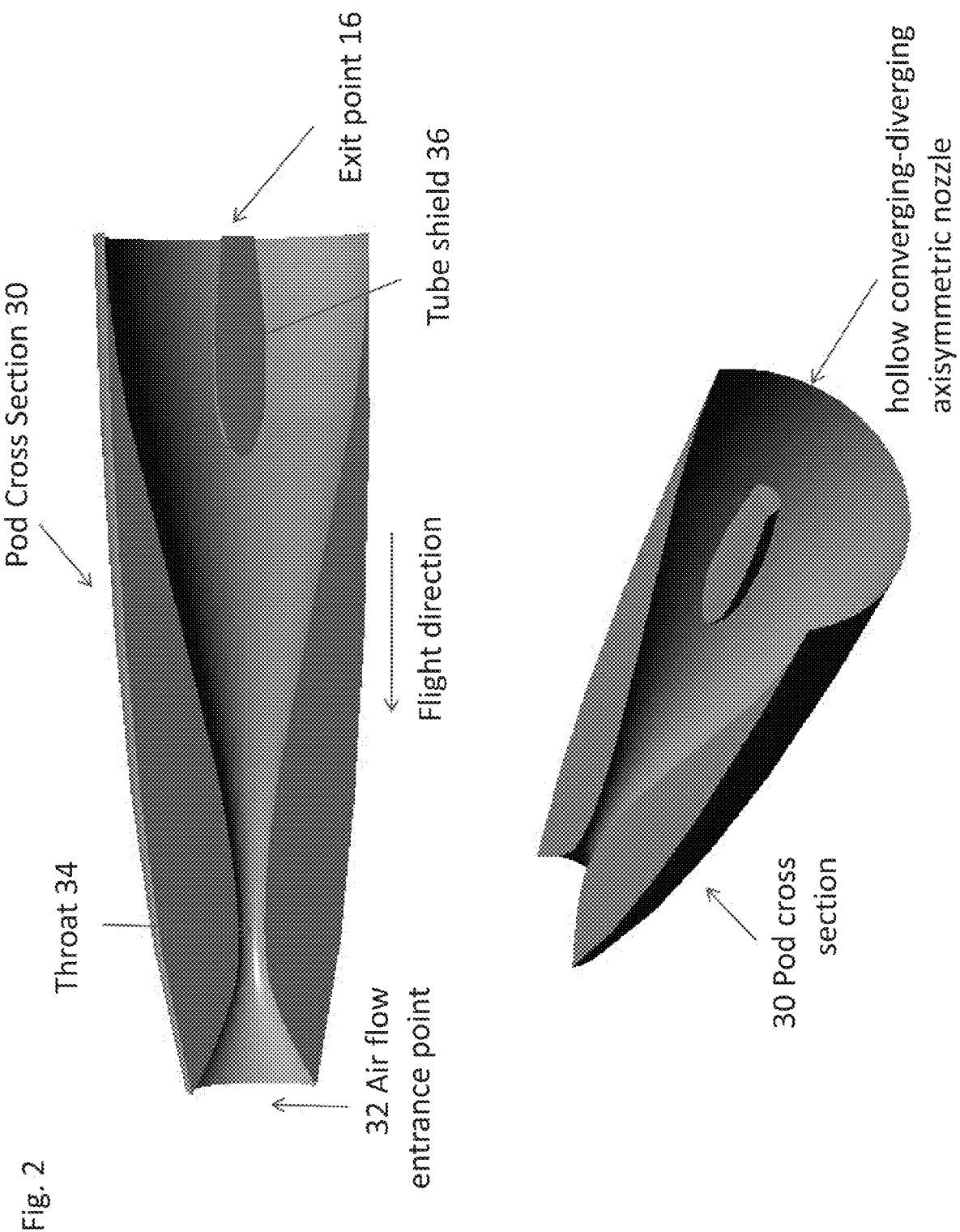
FIG. 2 is a simplified schematic view of a longitudinal cut along the axis of an axisymmetric pod for insect distribution.
Figure 10:
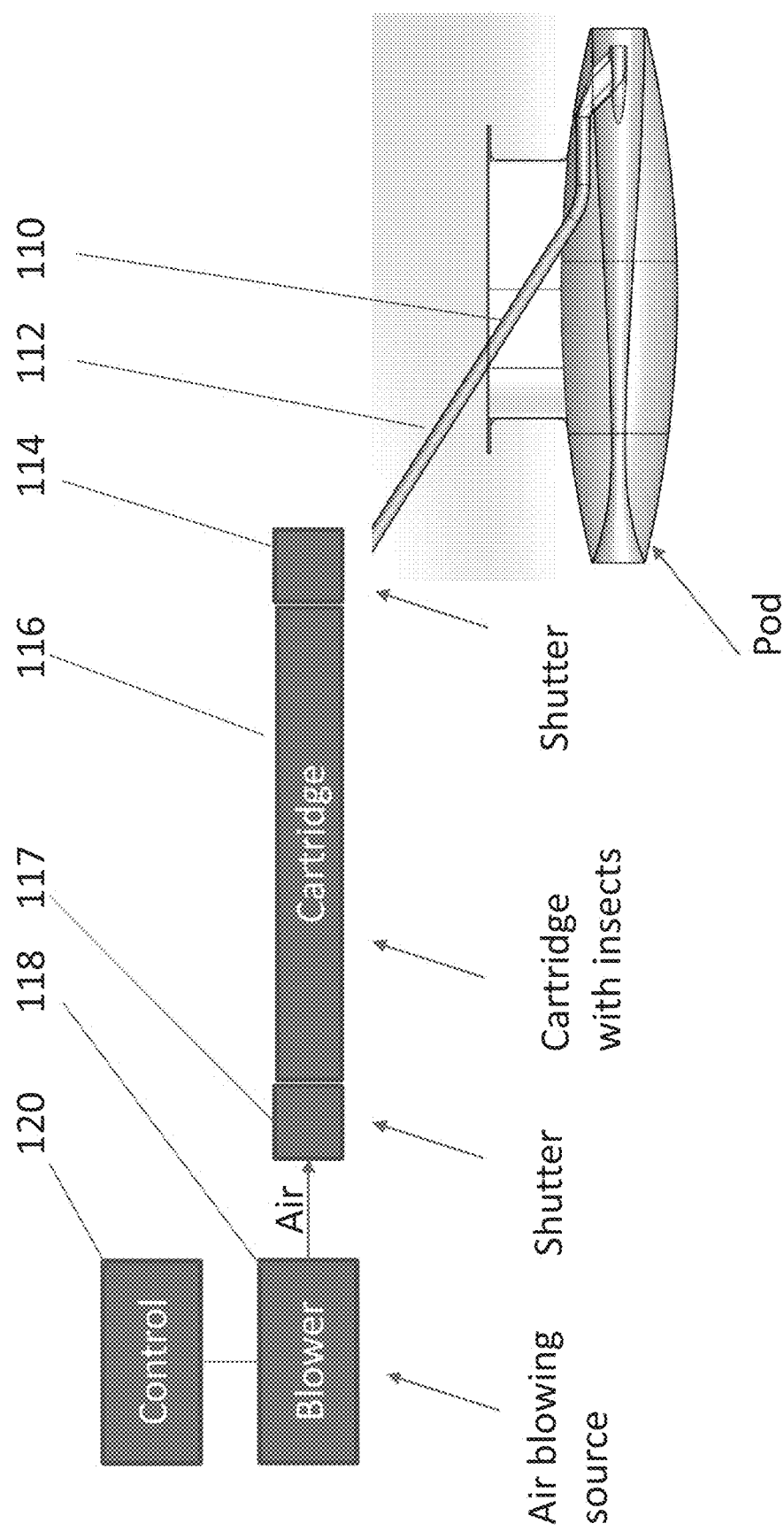
FIG. 10 is an illustration of the pod of FIG. 2, showing feeding of the insects into the pod using overpressure.

Referring now to FIG. 2 and the diffuser 10 may comprise a pod 30. Pod 30 comprises an air flow entrance point 32, a narrow throat 34 downwind of the entrance point, and a tube shield 36 downwind of the throat and at a location at which the pod widens after the throat. The tube shield sits in front of second end 16 of the pipe which is the exit point for the insects. More specifically, for one optimized embodiment, the exit is actually a few tens of millimeters upstream of the end of the pod external profile end, as shown in FIG. 10.

The pod cross section defines a profile surrounding the second end 16, which is designed to provide a steadily changing airspeed within the pod and provide the airflow equivalent of dead water at the exit point. Thus the opening at the second end 16 is located within the shaped profile of the pod at an airspeed minimum location.

Figure 3:
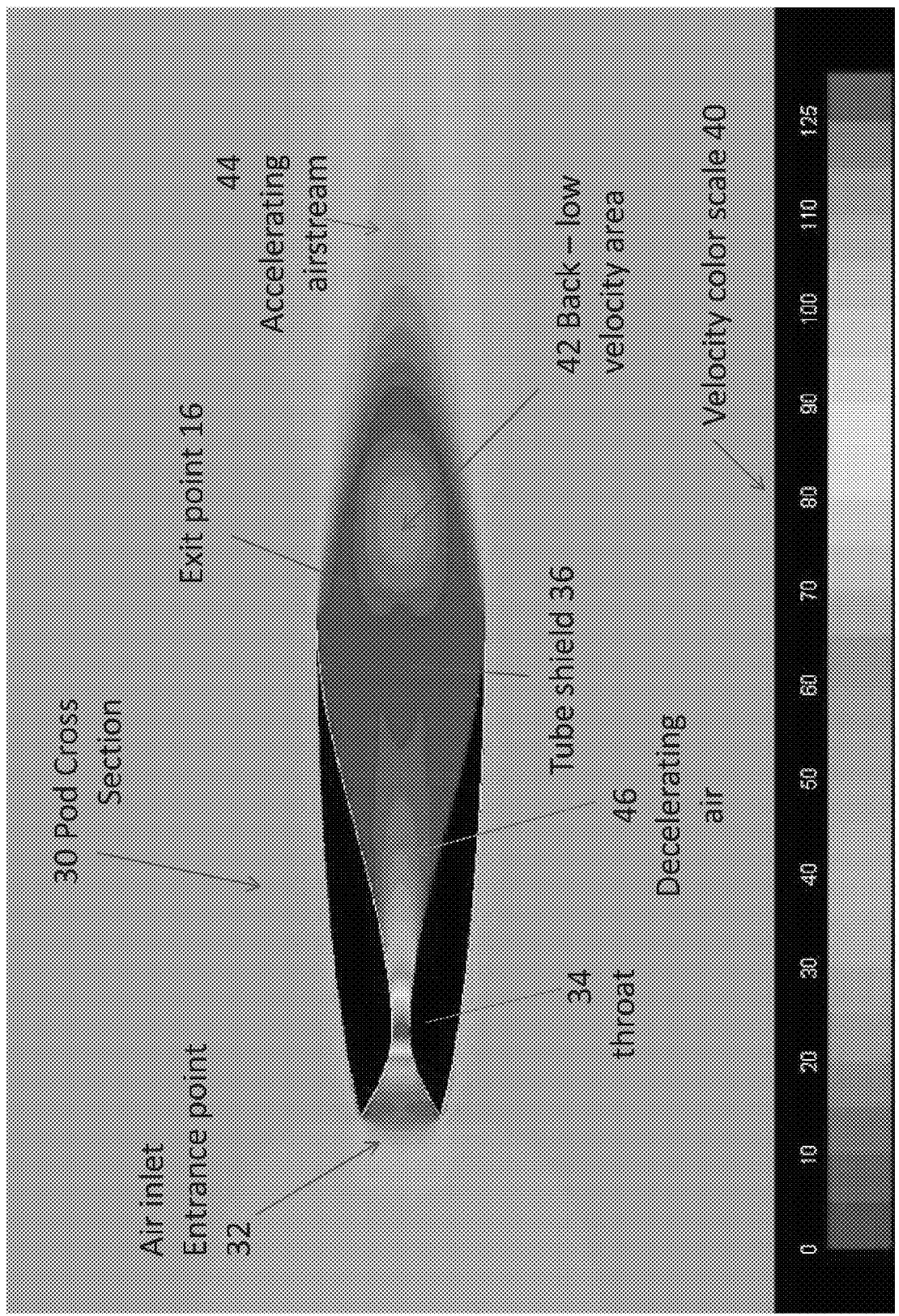
FIG. 3 is a simplified diagram showing simulated air velocities resulting from the axisymmetric pod shape of FIG. 2.

Reference is now made to FIG. 3 which shows the pod shape profile and different air speeds, shown in color according to the color scale 40. The parts of the pod profile are given the same reference numerals as in FIG. 2. Region 42 is a region of minimum airspeed around the exit point 16. The steadily changing airspeed may comprise a gradient of steadily increasing airspeed 44 away from the distribution tube in the direction away from the direction of travel of the aircraft. Furthermore, the profile is shaped to provide a region of gradual aerodynamic deceleration 46 towards the exit point 16 from the upstream end. The tube shield 36 is a blunt obstacle that is located upwind of the second end 16, to shield the second end and generate the low velocity area 42.

The shape of the pod may additionally form a nozzle surrounding the second end. Alternatively the end of the shield may be formed as a nozzle to surround the second end exit point. Returning to FIG. 2 and the tube shield may shield the second end. The tube shield 36 may have an aerofoil-shaped cross section to improve airflow around the exit point at the second end 16, and thus avoid causing drag. The tube cover and the nozzle opening of the pod may be considered to form the profile.

In an embodiment, the profile, or the profile combined with the mounting, may be shaped to define an airflow direction that is tangential to streamlines local to the second end of the pipe and the exit point.

The throat construction provides the pod with a subsonic converging-diverging nozzle structure. Alternatively, the pod may have a bi-cubic polynomial internal contour. Again, the pod may have an elliptical external shape.

The aerofoil shape of the tube shield may be a NACA standard shape, for example the NACA 0018 standard shape.

The tube shield 36 may be positioned within the pod so that a smooth external contour of the standard shape limits flow separation to the near wake of the blunt trailing edge section of the nozzle, thus causing the relatively still area around the immediate exit.

In a further alternative, the pod may have a cubic construction instead of being round in the transverse cross section.

The diffuser may be integrated into an aircraft pod.

Figure 4:
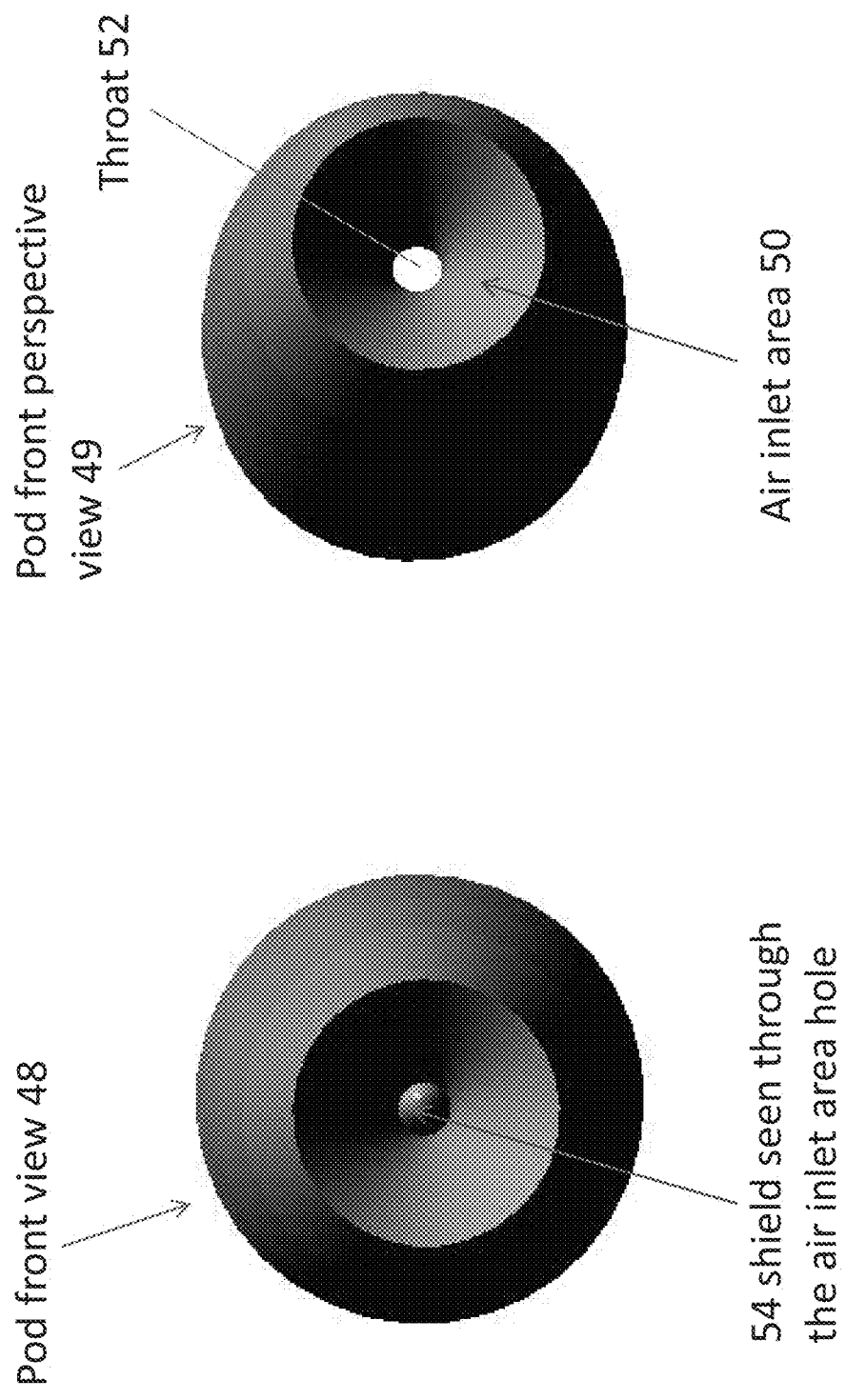
FIG. 4 is a schematic front view of an axisymmetric pod for insect distribution, according to an embodiment of the present invention.

Reference is now made to FIG. 4 which shows straight 48 and perspective 49 views of the pod from the front. A wide opening at air inlet area 50 leads to a narrow throat 52 and the tube shield 54 may be seen through the throat 52.

Figure 5:
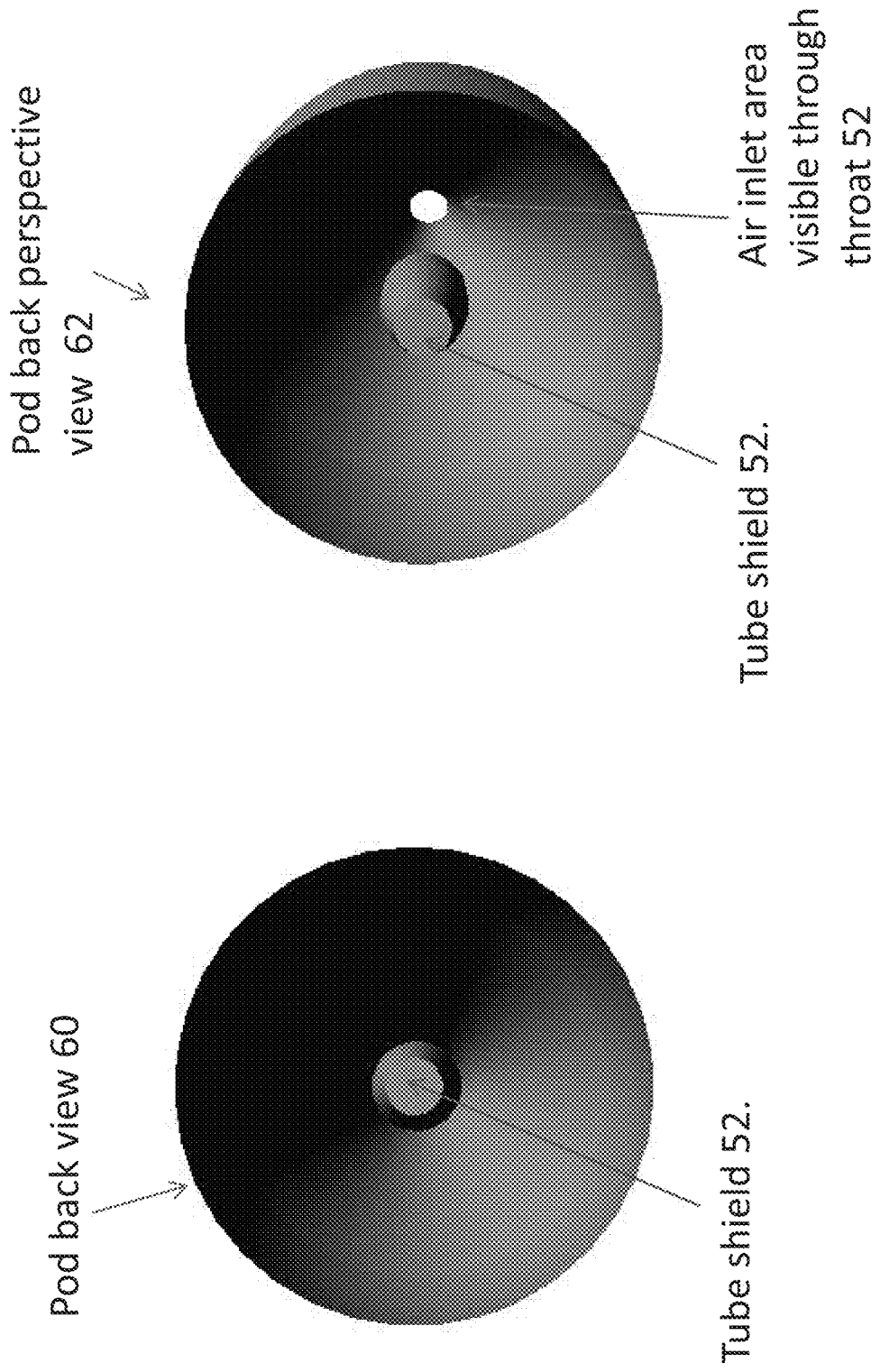
FIG. 5 is a schematic back side view of an axisymmetric pod for insect distribution according to an embodiment of the present invention.

Reference is now made to FIG. 5 which shows the same pod in straight 60 and perspective 62 views from the rear. In the perspective view, the air inlet is seen through the throat 52. In both views, the tube shield 54 is shown in front of the exit point.

As shown, the pod comprises a substantially circular transverse cross section.

Figure 6:
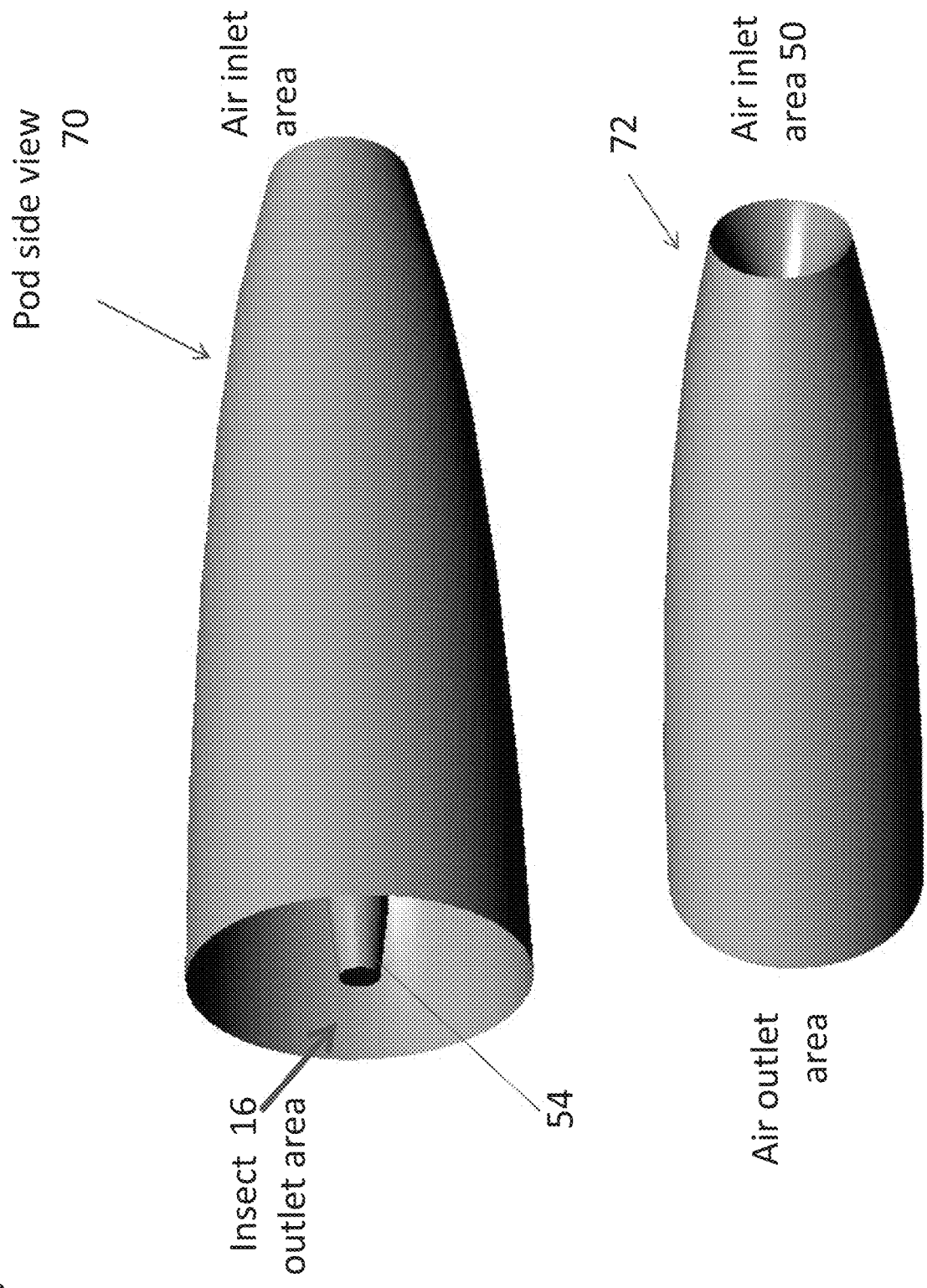
FIG. 6 is a schematic side view of an axisymmetric pod for insect distribution according to an embodiment of the present invention.

Reference is now made to FIG. 6 which shows left handed 70 and right handed 72 perspective views of the pod from the side. At one end is shown the air inlet area 50 and at the other end is shown the insect exit area at the second end 16 in front of the tube shield 54.

Figure 7:
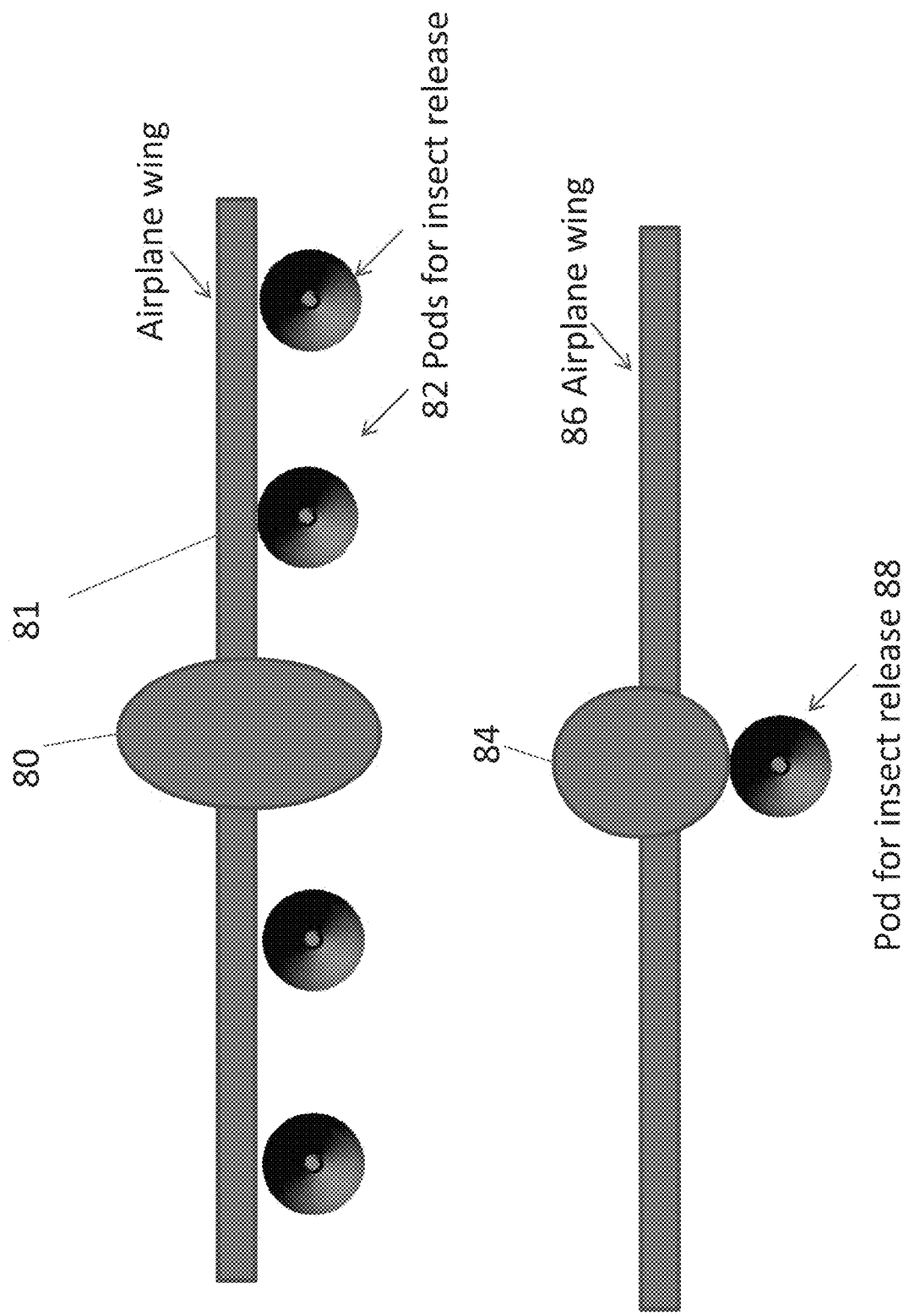
FIG. 7 is a schematic airplane back view with the axisymmetric pod shape of FIG. 2 mounted below the wings at several points.

Reference is now made to FIG. 7 which is a schematic diagram showing an aircraft 80 with wings 81 and with pods 82 arranged below the wings. In an alternative configuration, aircraft 84, with wings 86 has a single pod 88 mounted under the fuselage.

Figure 8:
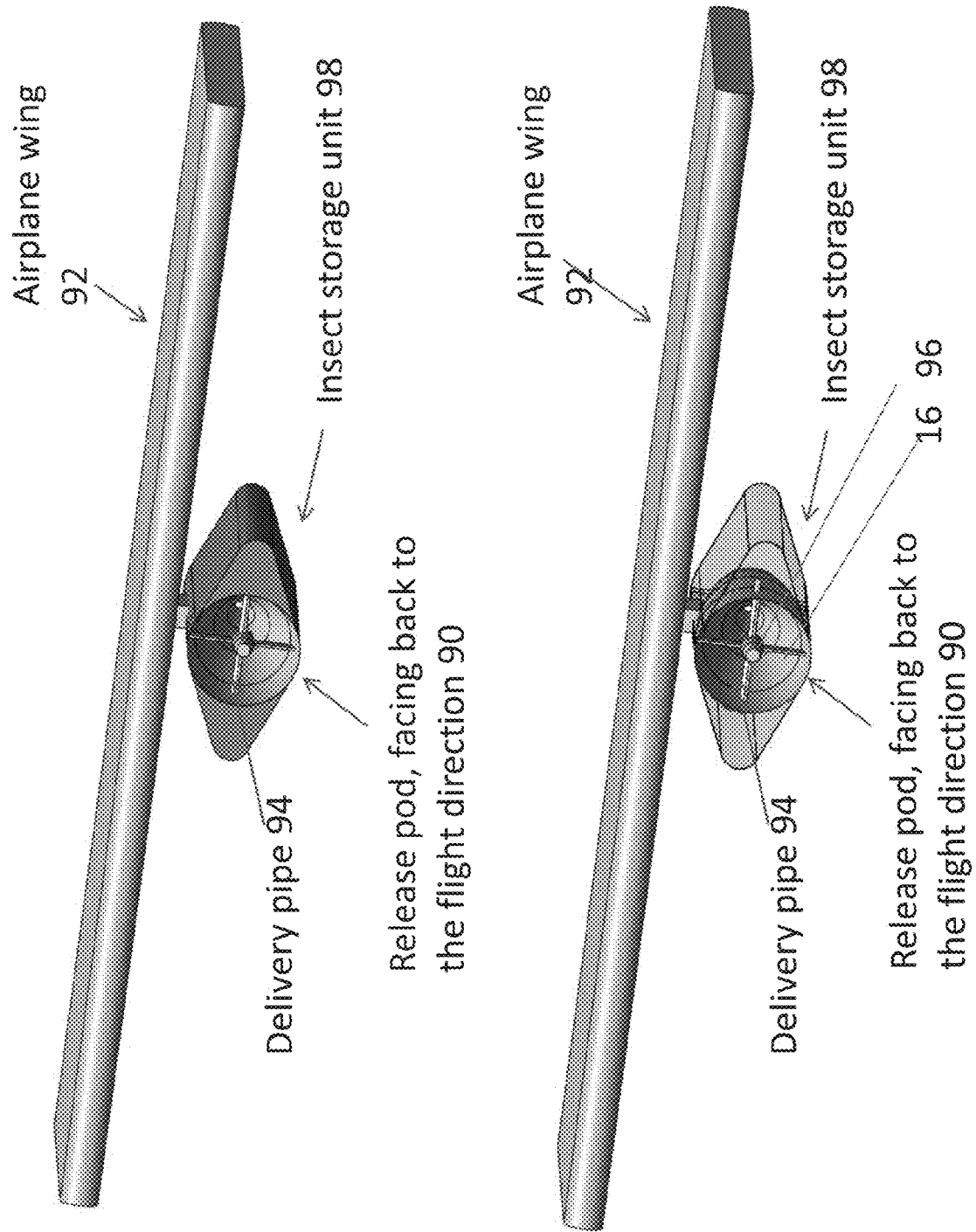
FIG. 8 is a schematic aeroplane wing view showing storage tanks for insects connected to the pod with aerodynamic structure, enclosing delivery pipes between the storage and the release point within the release pod.

Reference is now made to FIG. 8, which is a simplified schematic diagram illustrating how an insect storage unit may be built into a pod according to the present embodiments. The pod 90 is here from behind and is suspended under wing 92, although the same applies to the embodiment that is suspended under the fuselage. The pod has the same air intake and narrow throat as in the previous embodiments, and the exit area is likewise at second end 16 of delivery pipe 94, and is shielded by pipe shield or nozzle 96. The insect storage unit 98 or insect source, is built around the pod on the outside, to form the overall diffuser as a single structure.

Reference is now made to FIG. 9, which is a simplified diagram showing an alternative embodiment of the pod in which the insect storage units are mounted alongside the pod itself. Both the pod itself 100 and the insect storage units 102 are located under wing 104. Pipe 106 feeds the insects from the storage to the pod exit location. The pod is identical to previous embodiments with the narrow throat and pipe shield 108.

Reference is now made to FIG. 10 which shows a pod 110 receiving an insect feed from pipe 112. Shutter 114 allows the insect feed to be opened and closed, as the insects emerge from cartridge 116. Cartridge 116 receives blown air, as long as shutter 117 is open, from an air pressure source 118 under control of controller 120.

It is noted that in continuous feed embodiments, say where the insects are delivered via conveyor belt, the shutters may be dispensed with. The insect source is thus provided with an overpressure which gives the insects some velocity of their own when exiting the aircraft. A typical air velocity exiting the tube may be around 5 m/s (five meters per second).

Figure 11:
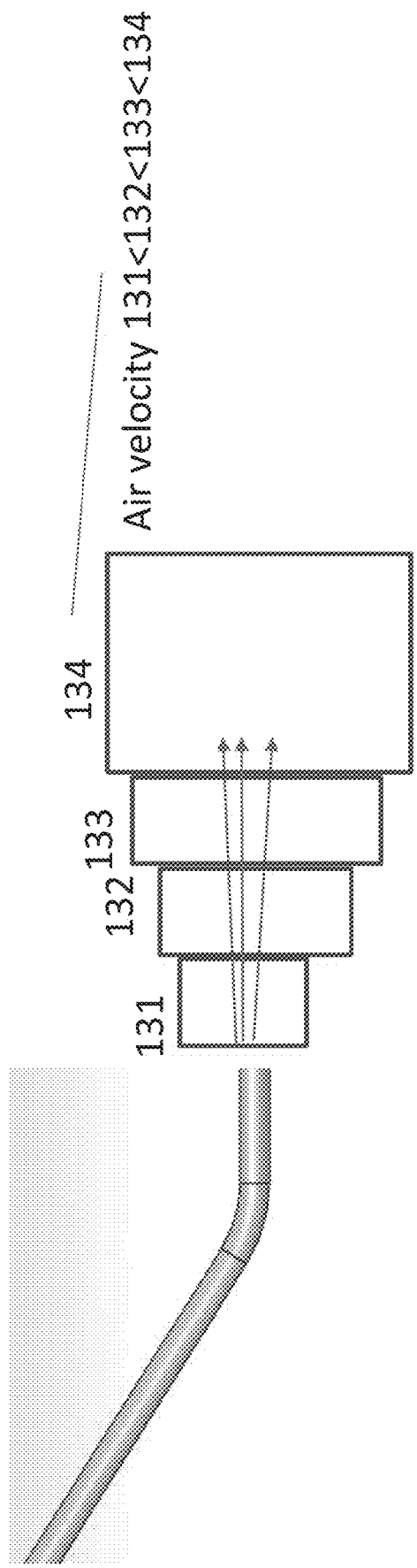
FIG. 11 is an illustration of a release pipe for use at low air velocities and showing how the insects may be released into the air stream and will be gradually brought up to the speed of the ambient air.

As mentioned above, for low airspeeds, not much structure is needed around the insect pipe, although the pipe may be aligned with the local airstream. FIG. 11 illustrates a system suitable for wind velocities between 10 and 20 m/s. Pipe 130 is followed by blocks 131, 132, 133 and 134. Each block represents a similar step increase in wind velocity and at these low velocities, even without specific structure, a stepped increase in wind velocity may be achieved.

Reference is now made to FIG. 12, which is a simplified diagram showing a minimal pod structure 140 which is suitable for air velocities of 20-30 m/s and a larger pod structure 142 which is suitable for air velocities above 30 m/s.

Figure 13B:
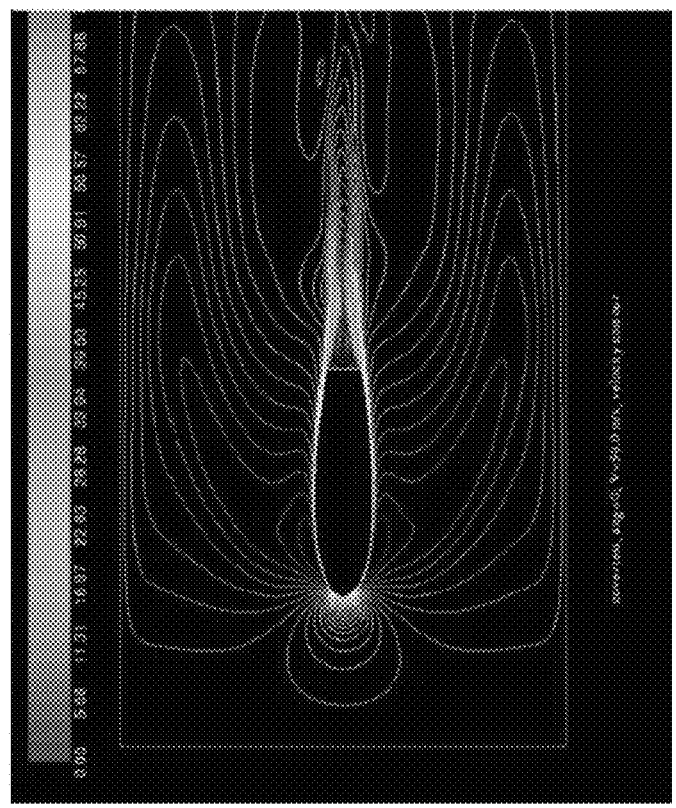
FIGS. 13A and 13B are simplified air speed diagrams in which the colors indicate regions of high and low airspeed.
Figure 13A:
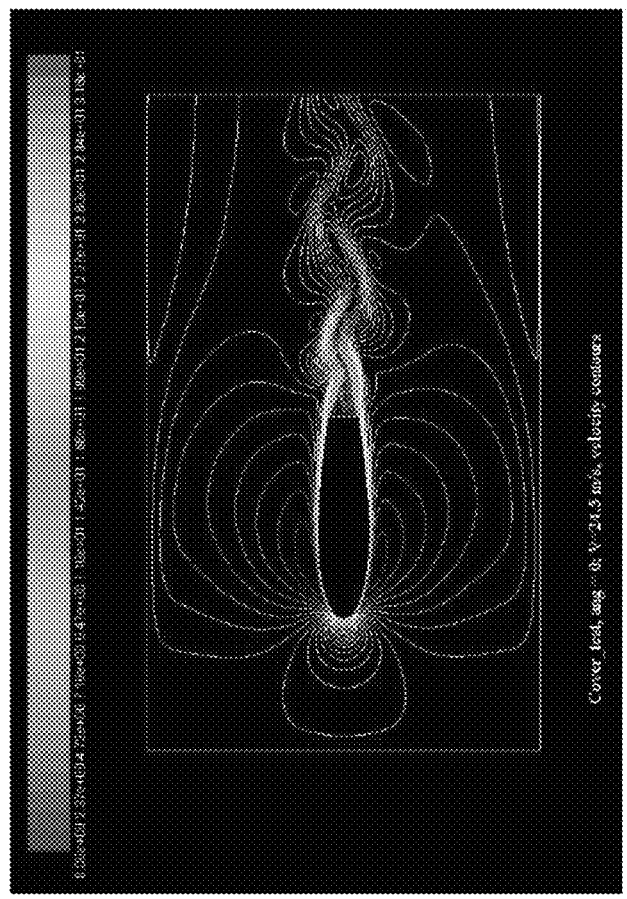

Reference is now made to FIGS. 13A and 13B, which are airflow diagrams showing airflow around the pod at different velocities. FIG. 13A shows airflow around the minimal pod 140 at an air velocity of 24.5 m/s and FIG. 13B shows airflow around the structure 140 at an airspeed of 59 m/s. At the lower airspeed the airflow is fairly chaotic but gets smoother towards the higher airspeed.

Figure 14:
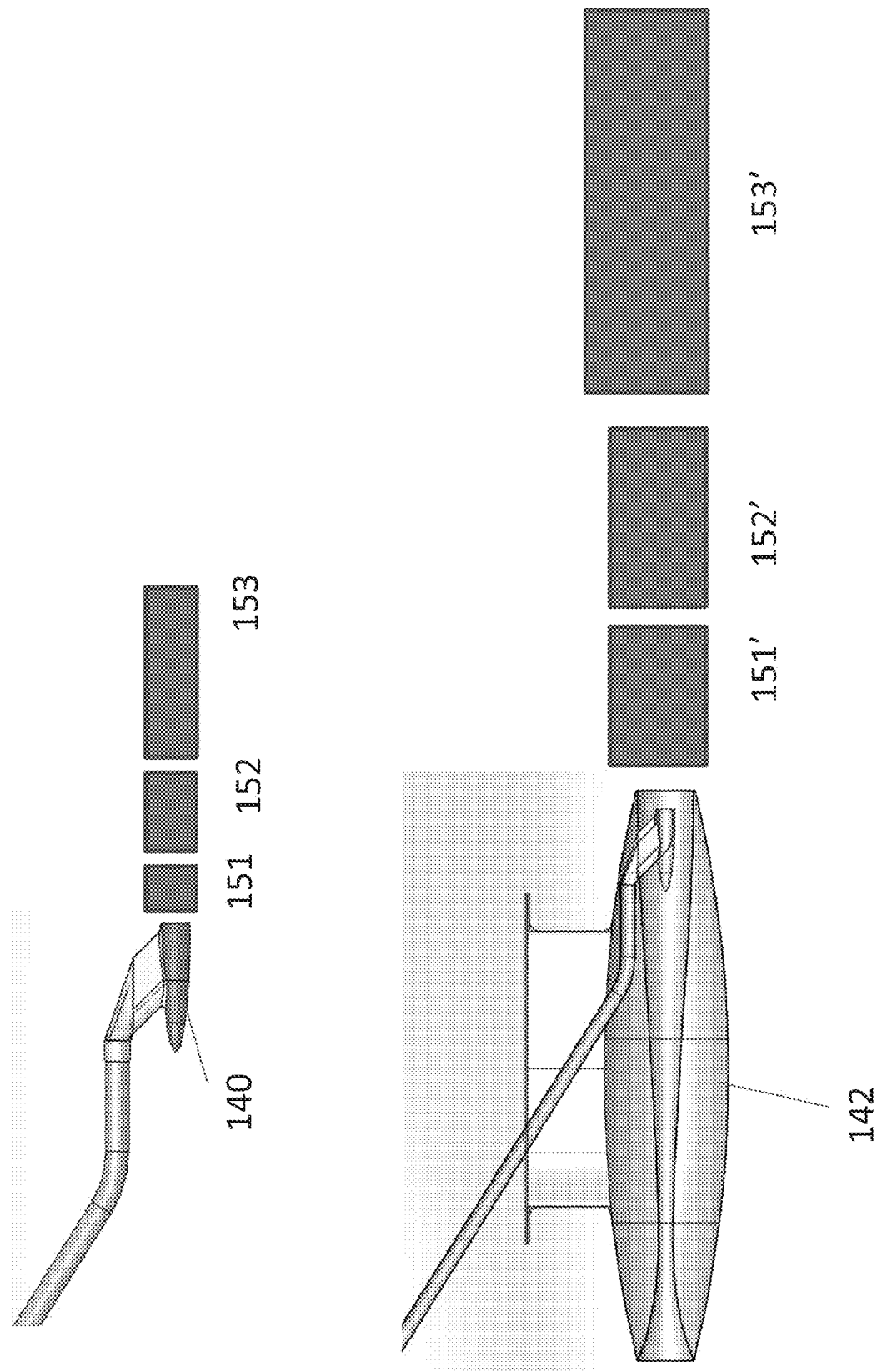
FIG. 14 is a simplified air speed diagram showing velocities as blocks of volume of equal size steps in velocity.

FIG. 14 illustrates the two structures 140 and 142 and shows the airflow in terms of blocks 151, 152, 153, 151', 152', 153', defining regions of air velocity step change. As shown, successive step changes get more gradual until the insects reach the ambient air.

Reference is now made to FIG. 15, which is a simplified schematic diagram illustrating an example of insect distribution using the present embodiments and pointing out actual velocities measured. The air velocity is 63 m/s. The insects are stored and a release device gives the insects a small release velocity. The structure of the pod ensures that there is a differential of no more than 15 m/s as the insects exit the pipe and then they are gradually speeded up to the ambient windspeed as they get further from the release point.

As discussed, the insects being distributed comprise relatively fragile insects being unable to bear a wind shear in excess of 60 km/h. The insects being distributed may be male insects, may be sterile males and may be sterile male mosquitoes.

The larger embodiments may be used to distribute insects from an aircraft travelling in excess of 140 kmh.

Additional comments on the pod geometry as are follows. The inner shape of the axisymmetric Pod geometry is essentially a converging-diverging nozzle. The specific nozzle may have been generated by matching two cubic polynomials, one for the converging section of the pod while the other is used for the diverging part.

To be more precise, each one of the nozzle parts has the general mathematical shape of:

$$r(x) = A^*x^3 + B^*x^2 + C^*x + D$$

The two sets of coefficients are uniquely defined from the conditions:

The diameters are: at intake $D_i$=0.120 m, at throat $D_i$=0.030 m, and at exit $D_e$=0.12 0. Moreover, the intake station is set as the relative longitudinal section: $x_i$=0,000 m, the throat at: $x_t$=0.260 m, and the exit section is located at: $x_e$=1.240 m. The two curves are smoothly tailored at the throat with common slope angle of zero.

The above described internal Pod example successfully reduces local air velocity to 10-15 m/s at the mosquito delivery station (four centimeters ahead of the exit section) while the aircraft flight speed is about 62-72 m/s. The mosquitoes in this example are delivered at a longitudinal ejection velocity of about 5 m/s.

If for any operational reasons, some kinds of insects are to be delivered at considerably higher flight speeds, the only action that need be taken is to gradually elevate the pressure inside the insect storage tanks, and consequently the ejection velocity may increase.

Regarding typical sizes, the overall length of a typical pod may be 1.24 m with the length of the converging section being 0.26 m and the diverging part being 0.98 m. A typical intake diameter is 0.12 m, a typical diameter for the throat is 0.03 m and a typical exit diameter is 0.12 m.

It is expected that during the life of a patent maturing from this application many relevant pods and delivery systems will be developed and the scope of the corresponding terms are intended to include all such new technologies a priori.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment, and the above description is to be construed as if this combination were explicitly written. Conversely, various features of the invention, which are, for brevity, described in the context of a single embodiment, may also be provided separately or in any suitable subcombination or as suitable in any other described embodiment of the invention, and the above description is to be construed as if these separate embodiments were explicitly written. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A diffuser for distributing insects from an aircraft, the aircraft having an inside and an outside and a direction of travel, and comprising: at least one distribution tube connected to an insect source at a first end and open to the outside to form an opening at a second end in a direction away from the direction of travel of the aircraft, for distribution of the insects, said at least one distribution tube comprising a portion between said first end and said second end, said portion extending in a direction substantially parallel to a top portion of said diffuser, said portion of the distribution tube being disposed within said top portion of said diffuser; and a profile surrounding said second end, the profile being shaped to widen from a narrow throat while extending continuously rearwards towards said second end, thereby to define a steadily changing airspeed which is relatively low at said second end, the diffuser further comprising a tube shield downwind of said throat at a point where said profile is widened with respect to said throat, said point being upstream of said second end.

2. The diffuser of claim 1, wherein said opening is located in respect of said shaped profile at an airspeed minimum location.

3. The diffuser of claim 1, wherein said steadily changing airspeed comprises a gradient of change in said airspeed in a direction away from said distribution tube in said direction away from the direction of travel of the aircraft.

4. The diffuser of claim 3, wherein said profile is shaped to provide gradual aerodynamic deceleration towards said second end followed by said gradient of steadily accelerating airspeed.

5. The diffuser of claim 3, wherein a blunt obstacle is located upwind of the second end, thus generating a minimum in said airspeed at said second end at a point between said gradual aerodynamic deceleration and said gradient of steadily accelerating airspeed.

6. The diffuser of claim 1, said profile comprising:
a nozzle shape surrounding the second end;
and wherein said tube shield surrounds the second end within the nozzle shape, the tube shield having an aerofoil-shaped cross section, the tube shield and the nozzle shape together forming said profile.

7. The diffuser of claim 1, being an aircraft pod.

8. The diffuser of claim 7, wherein said pod comprises a substantially circular cross section.

9. The diffuser of claim 7, wherein said pod is for mounting under an aircraft fuselage or under an aircraft wing.

10. The diffuser of claim 7, wherein the pod comprises a subsonic converging-diverging nozzle shape.

11. The diffuser of claim 7, wherein the pod comprises a bi-cubic polynomial internal contour.

12. The diffuser of claim 7, wherein the pod comprises an elliptical external shape.

13. The diffuser of claim 6, wherein the aerofoil-shaped cross section is an NACA standard shape.

14. The diffuser of claim 13, wherein the NACA standard shape is an NACA 0018 standard shape.

15. The diffuser of claim 6, wherein the tube shield is positioned within an aircraft pod such that an external contour of the standard shape limits flow separation to a wake of a blunt trailing edge section of the nozzle shape.

16. The diffuser of claim 1, wherein the insect source is provided with an overpressure.

17. The diffuser of claim 16, wherein the overpressure is such as to provide an air velocity exiting the tube at the second end of substantially 1 m/s (one meter per second).

18. The diffuser of claim 6, wherein the nozzle shape is a cubic shape.

19. The diffuser of claim 1, wherein the insects being distributed comprise relatively fragile insects being unable to bear a wind shear in excess of 60 km/h.

20. The diffuser of claim 1, wherein the insects being distributed comprise male insects.

21. The diffuser of claim 1, wherein the insects being distributed comprise sterile male mosquitoes.

22. The diffuser of claim 1, used to diffuse from an aircraft travelling in excess of 110 kmh.

* * * * *